United States Patent [19]

Miyake et al.

[11] Patent Number: 4,621,137
[45] Date of Patent: Nov. 4, 1986

[54] ALPHA-GLYCOSYL GINSENOSIDES

[75] Inventors: Toshio Miyake; Hiromi Hijiya, both of Okayama; Shinji Suzuki; Teruo Matsumoto, both of Tokyo, all of Japan

[73] Assignee: Kabushiki Kaisha Hayashibara Seibutsu Kagaku Kenkyujo, Okayama, Japan

[21] Appl. No.: 562,221

[22] Filed: Dec. 16, 1983

[30] Foreign Application Priority Data

Dec. 24, 1982 [JP] Japan .................. 57-225809

[51] Int. Cl.$^4$ .......................... C07H 15/20; C07J 9/00
[52] U.S. Cl. .......................................... 536/5; 424/16; 424/49; 426/546; 426/593; 426/590; 435/97; 536/6.3; 536/18.1; 536/18.2; 536/18.5; 536/128; 514/777
[58] Field of Search .................. 536/5, 6.3, 18.1, 18.2, 536/18.5, 128

[56] References Cited

U.S. PATENT DOCUMENTS

| | | | |
|---|---|---|---|
| 3,886,272 | 5/1975 | Parkhurst et al. | 536/5 |
| 4,189,471 | 2/1980 | Ponpipom et al. | 536/5 |
| 4,229,441 | 10/1980 | Bugianesi et al. | 536/5 |
| 4,335,113 | 6/1982 | Combier et al. | 536/5 |
| 4,339,442 | 7/1982 | Takemoto et al. | 536/5 |

OTHER PUBLICATIONS

Cai et al., "Chem Abst.", vol. 97, 1982, P. 212635(p).
Shao et al., "Chem. Abst.", vol. 97, 1982, P. 212636(q).
Han et al., "Chem. Abst.", vol. 98, 1983, P. 95532(k).
Cai et al., "Chem. Abst.", vol. 99, 1983, P. 28082(w).

*Primary Examiner*—Johnnie R. Brown
*Attorney, Agent, or Firm*—Browdy and Neimark

[57] ABSTRACT

The present invention relates to food products containing a novel alpha-glycosyl ginsenoside wherein one or more alpha-glucosyl moieties are bound to ginsenoside residue, and a process for producing the food products. Such alpha-glycosyl ginsenoside is obtainable by subjecting an aqueous solution of ginsenoside and an alpha-glucosyl saccharide to an alpha-glucosyl transferase.

4 Claims, 1 Drawing Figure

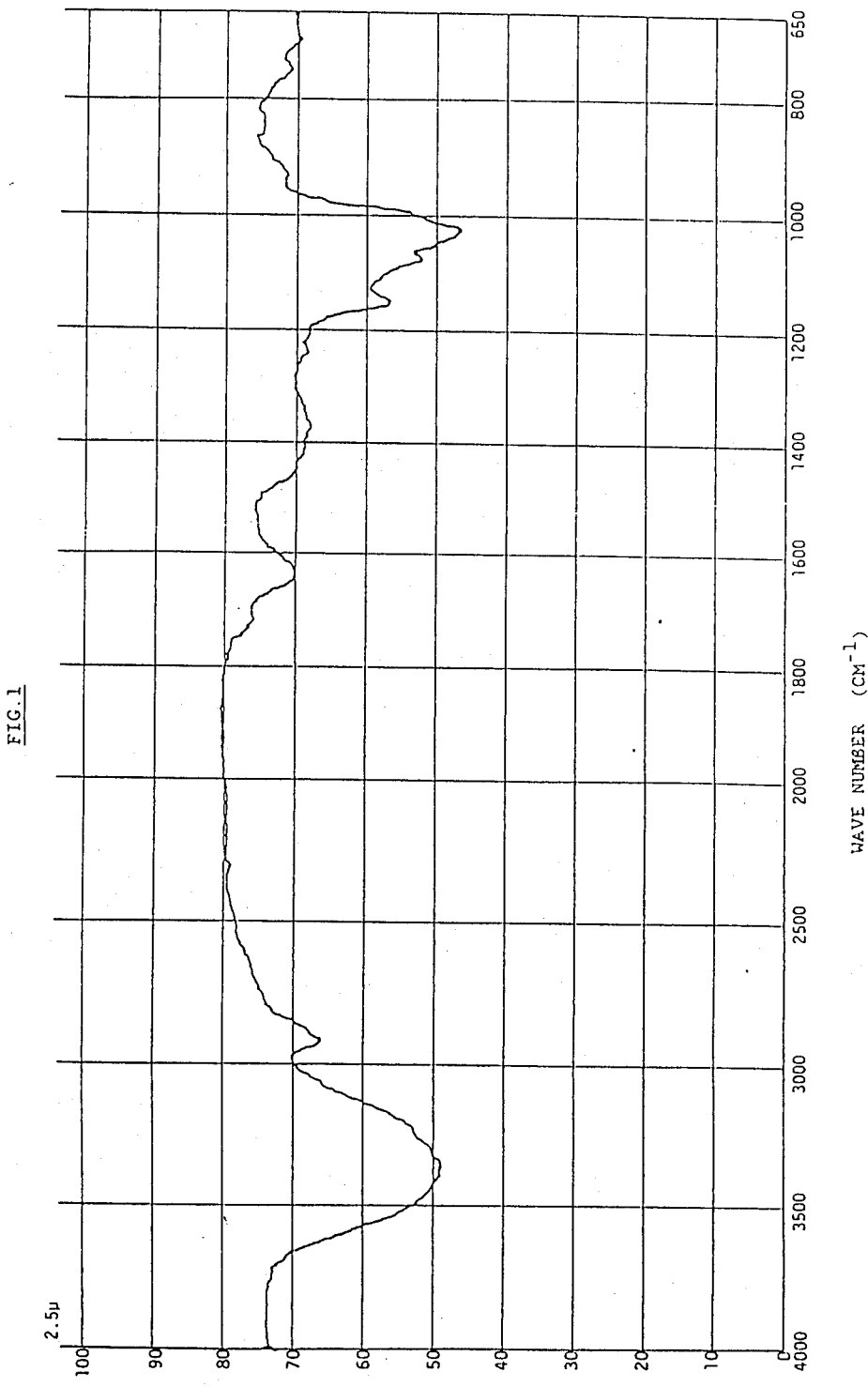

ALPHA-GLYCOSYL GINSENOSIDES

FIELD OF THE INVENTION

The present invention relates to food products and process for producing same. More particularly, it relates to food products containing a novel alpha-glycosyl ginsenoside wherein one or more glucosyl residues are bound to ginsenoside moiety in alpha-fashion, and a process for producing the food products.

DETAILED DESCRIPTION OF THE INVENTION

Ginseng or extract thereof has been utilized from ancient time in a health food or medicine administered internally to utilize its invigorating, peptic, intestine-regulating, haematic, anti-inflammatory or expectorant effect.

As reported in YAKUGAKU-ZASSHI, Vol. 98, No. 8, pp. 1,048–1,054 (1978), ginseng contains as its effective component a glycoside, so-called "ginsenoside". Ginsenoside is divided into two classes, i.e. ginsenoside-Ro and ginsenoside-Rx, according to the difference in chemical structure of aglycon. The chemical structures of ginsenoside-Ro and -Rx are as follows:

Chemical structure of ginsenoside-Ro

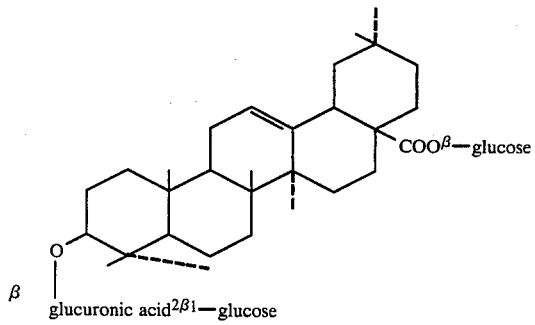

Chemical structure of ginsenoside-Rx

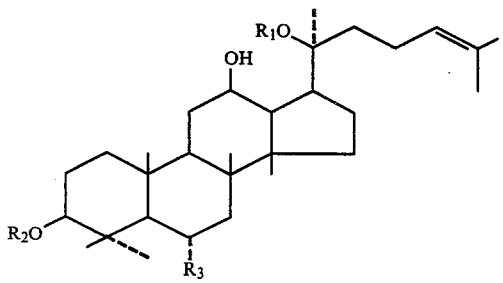

In addition to ginsenoside-Ro and -Rx, the following derivatives are documented:

Ginsenoside-Rb$_1$,
  $R_1 = -^\beta$glucose-$^{6\beta 1}$glucose,  $R_2 = -^\beta$glucose-$^{2\beta 1}$glucose, $R_3 = H$;
Ginsenoside-Rb$_2$,
  $R_1 = ^\beta$glucose-$^{6\alpha 1}$arabinopyranose, $R_2 = -^\beta$glucose-$^{6\beta 1}$glucose, $R_3 = H$;
Ginsenoside-Rc,
  $R_1 = -^\beta$glucose-$^{6\alpha 1}$arabinofuranose, $R_2 = -^\beta$glucose-$^{2\beta 1}$glucose, $R_3 = H$;
Ginsenoside-Rd,
  $R_1 = -^\beta$glucose, $R_2 = -^\beta$glucose-$^{2\beta 1}$glucose, $R_3 = H$
Ginsenoside-Re,
  $R_1 = -^\beta$glucose, $R_2 = H$, $R_3 = -O-^\beta$glucose-$^{2\alpha 1}$rhamnose;
Ginsenoside-Rf,
  $R_1 = R_2 = H$, $R_3 = -O-^\beta$glucose-$^{2\beta 1}$glucose
Ginsenoside-Rg$_1$;
  $R_1 = -^\beta$glucose, $R_2 = H$, $R_3 = -O-^\beta$glucose; and
Ginsenoside-Rg$_2$,
  $R_1 = R_2 = H$, $R_3 = -O-^\beta$glucose-$^{2\alpha 1}$rhamnose These ginsenosides are found in an extract obtained by treating a tissue or organ of ginseng (e.g. *Panax-ginseng* C. A. Meyer or *Gynostemma pentaphyllum*) with a solvent, e.g. water or alcohol. Generally, such extract or concentrate thereof is available as a "Ginseng Extract" for use in oral administration including ingestion.

Ginseng extract, however, exhibits inherent unpleasant tastes, such as, a strong astringent or harsh taste, as well as an intensive bitterness.

The present inventors have earnestly investigated means to eliminate the unpleasant tastes.

As a result, we discovered that ginsenoside is responsible for the bitter, astringent or harsh taste, and that these unpleasant tastes can be substantially eliminated by converting ginsenoside into an alpha-glycosyl derivative. Also, we found that the alpha-glycosyl ginsenoside is readily hydrolyzable into ginsenoside by an in vivo alpha-glycosidase, e.g. alpha-glucosidase. Based on these findings, we found that alpha-glycosyl ginsenoside can be produced and used similarly as ginsenoside without fear for its toxicity or additional medical efficacy. Thus, we established food products containing alpha-glycosyl ginsenoside, and process for producing the food products.

The term "food products" as used in this specification shall mean, in addition to foods and drinks in general, all products wherein taste is an important factor, e.g. liquors; tobacco; feeds and pet foods; cosmetics, such as, gargle, dentifrice and oral-refreshing agent; and drugs, such as those for internal administration and troche.

As regards alpha-glycosyl ginsenoside which may be used in the present invention, any alpha-glycosyl ginsenoside can be used regardless of its production process as long as it contains alpha-glycosyl ginsenoside in which one or more alpha-glucosyl residues are bound to the ginsenoside moiety.

A suitable process for producing alpha-glycosyl ginsenoside on an industrial-scale is a process which comprises subjecting an aqueous solution containing ginsenoside and an alpha-glycosly saccharide to an alpha-glucosyl transferase, and harvesting the resultant alpha-glycosyl ginsenoside.

As regards a usable ginsenoside, any crude and partially-purified ginseng extract containing a substantial amount of ginsenoside and producing alpha-glycosyl ginsenoside are equally suitable for use in the invention, as is a highly-purified ginsenoside.

The alpha-glucosyl saccharides suitable in the invention are those which allow an alpha-glucosyl transferase to form alpha-glycosyl ginsenoside from ginsenoside. Accordingly, the use of an appropriate substrate, i.e. alpha-glucosyl saccharides including partial starch hydrolysate or sucrose, which is susceptive to the transferase, is recommended to facilitate the formation of alpha-glycosyl ginsenoside. For example, in the case of using alpha-glucosidase (EC 3.2.1.20) as the alpha-glucosyl transferase, an alpha-glucosyl saccharide, such as malto-oligosaccharide including maltose, maltotriose and maltotetraose, partial starch hydrolysate having a Dextrose Equivalent (DE) of about 10–70, or sucrose, is preferable. When alpha-amylase (EC 3.2.1.1) is employed, the use of a gelatinized or partially hydrolyzed starch (dextrin) having a DE of below 1 or up to about 30 is suitable. For cyclodextrin glucanotransferase (EC 2.4.1.19), cyclodextrins or a gelatinized or partially hydrolyzed starch having a DE of below 1 or up to about 60 is suitable. Sucrose is suitable in a process using dextransucrase (EC 2.4.1.5).

Gelatinized or partially hydrolyzed starch which may be used in the invention is readily preparable from a starch which may be a tuberous or subterranian stem starch from potatoes or sweet potatoes; or a cereal starch from wheat or corn. In case a crude ginseng extract contains a substantial amount of starch, gelatinized or partially hydrolyzed starch may be omitted if necessary. The gelatinized starch may be prepared by heating a starch suspension at a temperature above its gelatinization temperature, generally, 70°–140° C. The partial starch hydrolysate may be obtained by hydrolyzing a starch to a desired DE level with the aid of acid or amylase. Of course, two or more members of the alpha-glucosyl saccharides may be used in combination.

A usable alpha-glucosyl transferase may be those which act on an aqueous solution containing an appropriate alpha-glucosyl saccharide and ginsenoside, and form alpha-glycosyl ginsenoside without decomposition of the ginsenoside. For example, alpha-glucosidase (EC 3.2.1.20) derived from animal, such as that from pig liver, plant, such as those from buckwheat seed, fungi, such as, e.g. those from genus Mucor or Penicillium, or yeast, such as, e.g. those from genus Saccharomyces; alpha-amylase (EC 3.2.1.1) derived from various microorganism, especially, a bacterium of genus Bacillus or a fungi of genus Aspergillus; cyclodextrin glucanotransferase (EC 2.4.1.19) derived from a bacterium, such as, e.g. those from genus Bacillus or Klebsiella; dextransucrase (EC 2.4.1.5) derived from a bacterium, such as, e.g. those from genus Leuconostoc; dextran dextrinase (EC 2.4.1.2) derived from a bacterium, such as, e.g. those from genus Acetobacter; amylosucrase (EC 2.4.1.4) derived from a bacterium, such as, e.g. those from genus Neisseria, are all advantageously usable in the invention.

The above described alpha-glucosyl transferase may not be necessarily purified prior to its use, and alpha-glycosyl ginsenoside is generally attainable with the use of a crude enzyme, provided that the enzyme satisfies the hereinbefore described requirements. For example, in the case of using an animal or plant enzyme, a satisfiable crude alpha-glucosyl transferase may be prepared either by salting-out an extract from a minced animal or plant tissue using ammonium sulfate, or by precipitating the extract using an organic solvent, such as alcohol or acetone, to effect separation. If necessary, the obtained crude enzyme may be further purified with conventional procedure prior to its use.

In the production of the desired enzyme from a microorganism, a solid culture, such as wheat bran culture, or a liquid culture such as those using a fermenter is generally carried out. Preparation of an alphaglucosyl transferase using solid culture may be carried out by extracting similarly as in the case of animal or plant enzyme, and the resultant crude enzyme may be, if necessary, purified in usual way prior to its use. In the case of using an alpha-glucosyl transferase obtained by a liquid culture, although the culture broth can be used intact in the invention, an supernatant containing the desired enzyme but free from insoluble substance is generally used. Occasionally, an enzyme in the whole cell may be used intact, or after extraction therefrom. Of course, a much more purified or commercially-available alpha-glucosyl transferase may be also used in the invention. Furthermore, the enzymatic reaction by alpha-glucosyl transferase can be effected continuously or batch-wise with the use of an immobilized alpha-glucosyl transferase. Also, alpha-glycosyl ginsenoside may be formed by culturing a microorganism or a tissue, such as those of animal or plant, on a culture medium containing an alpha-glucosyl saccharide and ginsenoside.

Suitable reaction conditions are those under which the alpha-glucosyl transferase acts on an aqueous solution containing ginsenoside and alpha-glucoside. Generally, ginsenoside and the alpha-glucosyl saccharide are dissolved together in water to give respective concentration of about 0.1–30 w/w % and about 1–50 w/w %, and also to give a preferred weight ratio of alpha-glucosyl saccharide to ginsenoside of about 0.5–300. As regards the reaction pH and temperature used for the enzymatic reaction, any pH and temperature can be employed as long as the alpha-glucosyl transferase acts on the given substrate to form alpha-glycosyl ginsenoside. Generally, a pH in the range of 3–10 and a temperature in the range of 20°–80° C. are suitable.

Dependent upon the varieties of food products, the resultant reaction mixture containing alpha-glycosyl ginsenoside may be used as a food product intact, or purified prior to its use if necessary. For example, after heat-inactivation of the enzyme accompanying filtration, the resultant filtrate may be allowed to contact with a magnesia adsorbent, e.g. "Neucillin", "Neucillin A", or "Columnlite", products of Fuji Chemial Industry incorporation, Ltd., Toyama-ken, Japan, "Tomix Granular" or "Tomix-S Granular", "Neoalumin" or "Neoalumin S", products of Tomita Phamaceutical Co., Ltd., Naruto-shi, Tokushima-ken, Japan, "M-511", a product of Hokkaido Soda Co., Ltd., Tokyo, Japan, both to adsorb and to remove coloring impurities, and the non-adsorbed liquid is harvested. The liquid may be concentrated into syrup, or, further, dried or pulverized into powder, prior to its use in food product.

If a much higher purification is desirable, alpha-glycosyl ginsenoside and impurities may be separated according to the differences in adsorbability by the use of a synthetic macroreticular resin, e.g. "Diaion HP-10", "Diaion HP-20" or "Diaion HP-40", products of Mitsubishi Chemical Industries Ltd., Tanashi, Tokyo, Japan, "Amberlite XAD-1", "Amberlite XAD-4", "Amberlite XAD-7" or "Amberlite XAD-8", products of Rohm & Haas Company, Philadelphia, Pa., USA, or "Imac-Syn-42", "Imac Syn-44" or "Imac Syn-46", products of Industrie de Maatshappily activate N.V., Amsterdam, Netherland. For example, if separation of free saccharide from ginsenoside compounds including alpha-glycosyl ginsenoside and the remaining ginsenoside is desirable, the reaction mixture is first applied on the above described magnesia adsorbent to remove coloring impurities, then further on a column of a synthetic macroreticular resin, whereby the compounds are adsorbed thereon while the saccharide is eluted. Thereafter, the adsorbed ginsenoside compounds are eluted therefrom by charging thereto a low alcohol solution, e.g. 40 v/v % aqueous ethanol solution, and concentrated into a syrup which may be dried and pulverized to harvest a powder.

Furthermore, by applying a solution containing alpha-glycosyl ginsenoside and remaining ginsenoside on a column of a synthetic macroreticular resin to allow ginsenoside to selectively adsorb thereon, an alpha-glycosyl ginsenoside preparation having a much higher purity can be harvested from the non-adsorbed part. Such preparation may be, if necessary, further purified and deionized with an ion exchange resin, e.g. strongly-acidic ion exchange resin (OH-form) or weakly-anionic ion exchange resin (H-form), or chromatographed to harvest a desired fraction, prior to its use.

Since, unlike ginsenoside, the alpha-glycosyl ginsenoside obtained in this manner is almost free from unpleasant tastes, i.e. bitter, astringent or harsh taste, it may be feasible as a food product alone, or in combination with other ingredient(s), regardless of its purification degree or purity.

Furthermore, since alpha-glycosyl ginsenoside is easily hydrolyzable into ginsenoside by in vivo alpha-glycosidase, such as alpha-glucosidase, it is advantageously feasible similarly as ginsenoside without fear for its toxicity or additional medicinal efficacy in a use wherein the inherent properties of ginsenoside, such as, invigorating, peptic, intestine-regulating, haematic, anti-inflammatory and/or expectorant effects, are desired. Accordingly, a food product containing alpha-glycosyl ginsenoside is advantageously feasible as a food product directed to improvement, maintenance or restoration of health. Thus, in addition to food products in general, e.g. seasoning, confectionaries, frozen desserts, syrups, processed fruits or vegetables, pickles or pickled products, processed meats or fish meat, delicacies, canned or bottled foods, liquors, soft drinks, or convenient foods or mixes, the concept "food products" according to the invention shall be extended to various products in solid, paste or solid, such as, feeds and pet foods for domestic animal or fowl, or fish, tobaccos, cosmetics and drugs including dentifrice, lipstick, lipcream, medicine for internal administration, troche, cod liver oil drop, oral refreshing agent or gargle, as long as taste is an important factor therein. The medicinal efficacy of alpha-glycosyl ginsenoside in these food products may be enhanced by incorporating thereto one or more substances, e.g. crude drug or medicine including those for promoting nutrition.

As regards the procedure by which alpha-glycosyl ginsenoside is prepared into, or added to such food products, conventional procedure can be employed in the invention as long as the food products can be prepared with, or added with alpha-glycosyl ginsenoside before completion of their processing; for example, by mixing, kneading, dissolving, soaking, permeating, spraying, coating and injection.

The alpha-glycosyl ginsenoside according to the invention will be explained hereinafter with reference to some experiments.

EXPERIMENT 1

Preparation of alpha-glycosyl ginsenoside

EXPERIMENT 1—1

Preparation of an alpha-glucosyl transferase

A seed culture of *Bacillus stearothermophilus* FERM-P No. 2222 was inoculated on 10 liters of a sterilized liquid medium, consisting of 2 w/v % soluble starch, 1 w/v % $NH_4NO_3$, 0.1 w/v % $KH_2PO_4$, 0.05 w/v % $MgSO_4.7H_2O$, 0.5 w/v % corn steep liquor, 1 w/v % $CaCO_3$ and water, and cultured thereon at 50° C. for 3 days aeration-agitation conditions. After completion of the culture, the culture broth was centrifuged, and the supernatant was added with ammonium sulfate to give a 0.7 saturation and also to effect salting-out, obtaining a crude enzyme preparation having an about 80,000 units of cyclodextrin glucanotransferase (EC 2.4.1.19).

One unit of cyclodextrin glucanotransferase activity is defined as the amount of enzyme that completely eliminates the iodine development of 15 mg soluble starch upon enzymatic reaction under the following conditions: To 5 ml of a 0.3 w/w % soluble starch solution in 0.02M acetate buffer (pH 5.5.), containing $2 \times 10^{-3}M$ calcium chloride, is added 0.2 ml of a dilute enzyme solution, and the mixture is incubated at 40° C. for 10 minutes. Thereafter, 0.5 ml of the reaction mixture is added to 15 ml of 0.02N sulfuric acid to suspend the enzymatic reaction, and the mixture is admixed with 0.2 ml of 0.1N $I_2$-KI solution to effect iodine development. Then, the absorbance of the mixture is determined at a wave length of 660 nm.

EXPERIMENT 1-2

Enzymatic reaction

One hundred and forty g of "KORAI-NINJIN EKISU", trade name of a commercially-available ginseng extract, available from Lotte Bussan Co., Ltd., Tokyo, Japan, and 500 g of maltodextrin (DE 20) were dissolved together in 500 ml of hot water. After adjusting to pH 6.0, the solution was added with 5,000 units of the above described crude cyclodextrin glucanotransferase, and incubated for 24 hours while maintaining pH 6.0 and 60° C. to effect enzymatic reaction. After keeping the reaction mixture at 95° C. for 10 minutes to inactivate the enzyme, the resultant, Sample No. 3 in Table I, was filtered, concentrated in vacuo at a temperature below 70° C., and dried to obtain a powder, Sample No. 4 in Table I.

Samples No. 1 and No. 2, controls, were prepared similarly as above by dissolving 100 g of the ginseng extract together with or without 500 g maltodextrin in 5 liters of water while heating, and incubating the resultant mixture in the absence or presence of a thermally-preinactivated 5,000 units of the cyclodextrin glucanotransferase.

Respective formulations of the Samples are given in Table I.

TABLE I

| | Sample No. 1* | Sample No. 2* | Sample No. 3** | Sample No. 4** |
|---|---|---|---|---|
| Formulation | Ginseng extract 100 g | Ginseng extract 100 g + Maltodextrin 500 g + Thermally-preinactivated | Ginseng extract 100 g + Maltodextrin 500 g + Active 5,000 units of the | Ginseng extract 100 g + Maltodextrin 500 g + Active 5,000 units of the |

TABLE I-continued

| | Sample No. 1* | Sample No. 2* | Sample No. 3** | Sample No. 4** |
| --- | --- | --- | --- | --- |
| | | 5,000 units of the enzyme | enzyme | enzyme |

Note:
*control; and
**present invention.

EXPERIMENT 2

Comparison test

An aqueous solution was prepared by dissolving Sample No. 4 in water to give the same concentration of Sample No. 3. Thereafter, an organoleptic test using aqueous solutions of Samples No. 1 through No. 4 was carried out at 25° C. with 20 panel members, and, by the panel, the most desirable and the most undesirable preparations were chosen along with comments on their taste qualities. The results are given in Table II.

As is apparent from Table II, the superiority of Samples No. 3 and No. 4 against Samples No. 1 and No. 2 in taste quality is obvious. The unpleasant taste or lingering after-taste of conventional ginseng extract or its mixture with saccharides was eliminated in the present alpha-glycosyl ginseng extract. Accordingly, the present ginseng extract has a decided advantage over them that the present ginseng extract is ingestable intact.

TABLE II

| Judgement | Sample No. 1* | Sample No. 2* | Sample No. 3** | Sample No. 4** |
| --- | --- | --- | --- | --- |
| Most desirable | 0 | 0 | 10 | 10 |
| Most undesirable | 11 | 9 | 0 | 0 |
| Taste quality | Strong bitter, astringent and harsh tastes linger to give an undesirable after-taste. | | Almost free from bitter, astringent or harsh taste not to give an undesirable after-taste. | |

Note:
*control; and
**present invention

EXPERIMENT 3

Identification of alpha-glycosyl ginsenoside

To an aqueous solution, prepared by dissolving 50 g of Sample No. 4, prepared in EXPERIMENT 1-2, in 100 ml of water, was added 2 g of "M-511", trade name of a commercial magnesia adsorbent, a product of Hokkaido Soda Co., Ltd., Tokyo, Japan, and the mixture was subjected to 30-minute standing under gentle stirring conditions, followed by filtration. Thereafter, the filtrate was applied on a 200 ml column of "Diaion HP-20", trade name of a commercial synthetic macroreticular resin, a product of Mitsubishi Chemical Industries, Incorporation, Tokyo, Japan, and the column was washed with water in an amount sufficient to remove free saccharides. Then, 2,000 ml of a 50 v/v % aqueous methanol solution was charged thereto to elute the ginsenoside compounds including alpha-glycosyl ginsenoside therefrom, and the eluate was concentrated, dried and pulverized to obtain about 7 g of a powder, Sample No. 5.

Sample No. 5 is a odorless, readily water-soluble and almost neutral substance in white powder form which has a slight bitter, astringent or harsh taste. This Sample is partially soluble in a low alcohol, such as methanol, ethanol or n-butanol, but hardly in chloroform or ethyl ether. An infrared spectrum of Sample No. 5 obtained according to the KBr tablet method is given in FIG. 1.

A small amount of Sample No. 5 in a minimum amount of water was subjected to a commercial crystalline glucoamylase (EC 3.2.1.3) at 50° C. in 0.02M acetate buffer (pH 5.0) to effect enzymatic reaction. In the course of the reaction, small amounts of the reaction mixtures were periodically sampled, and spotted on "Kieselgel 60", trade name of a commercial thin-layer plate, a product of Merck & Co., Inc., Rahway, N.J., USA, followed by ascending development using a solvent mixture of n-butanol, ethyl acetate and water (4:1:5). After drying the thin-layer plate, it was sprayed with 1% $Ce(SO_4)_2$ solution in 10% sulfuric acid, and allowed to develop at 100° C. for 10 minutes under heat-drying conditions. D-glucose, and a purified ginsenoside, used as controls, obtained from Sample No. 1 similarly as Sample No. 5 from Sample No. 4, were spotted and developed on the same thin-layer plate.

As a result, while a series of spots at $R_f$ 0.84, 0.67, 0.52, 0.41, 0.33, 0.29, 0.22, 0.19 and 0.11 which correspond to Ginsenoside-Ro, $-Rb_1$, $-Rb_2$, -Rc, -Rd, -Re, -Rf, $-Rg_1$ and $-Rg_2$ were found in the chromatogram of the ginsenoside, a newly-formed relatively large spot at $R_f$ near 0.36, small spot at $R_f$ near 0.24, and an unseparable tailing from origin to $R_f$ near 0.24 were found in the chromatogram of Sample No. 5, in addition to several undistinguishable or small spots corresponding to ginsenoside-$Rb_1$, $-Rb_2$ and -Re. The newly-formed spots and tailing equally appeared purple red as did ginsenoside.

Accordingly it can be concluded that Sample No. 5 is a mixture of a small amount of remaining ginsenoside and a series of novel substances corresponding to $R_f$ near 0.36 spot, $R_f$ near 0.24 spot and the unseparable tailing from origin to $R_f$ near 0.24 which are formed by the alpha-glucosyl transferase.

Sample No. 5 was subjected to glucoamylase, and the reaction mixture was periodically sampled and chromatographed similarly as above. As a result, the series of novel substances corresponding to the new spots and tailing were found to be gradually hydrolyzed in the course of the reaction, and to finally give a series of purple red spots corresponding to ginsenoside-Ro, $-Rb_1$, $-Rb_2$, -Rc, -Rd, -Re, -Rf, $-Rg_1$ and $-Rg_2$, and a brown spot at $R_f$ near 0.13 corresponding to D-glucose. The resultant hydrolysate exhibited astringent, bitter and harsh tastes similar to those of ginsenoside.

Separately, Sample No. 5 was subjected to a partially-purified alphaglucosidase from a pig liver extract, and the reaction mixture was chromatographed. As a result, it was confirmed that the novel substances in Sample No. 5 are easily hydrolyzable by the enzyme into ginsenoside and D-glucose, as in the case of using glucoamylase.

Based on the above described experimental results, it can be concluded that the novel substances, formed by alpha-glucosyl transferase, are those wherein one or more D-glucose moieties are bound to ginsenoside residue in alpha-fashion. This suggests that alpha-glycosyl ginsenoside is easily hydrolyzable in vivo into ginsenoside and D-glucose when ingested.

Also, unlike ginsenoside, Sample No. 5 hardly tastes bitter, astringent or harsh as Sample No. 3 or No. 4.

Accordingly, it can be also concluded that removal or elimination of the unpleasant tastes, such as bitter, astringent and harsh tastes, from ginsenoside, which is one of the present objects, is attainable by subjecting an aqueous solution containing ginsenoside and alpha-glucosyl saccharide to an alpha-glucosyl transferase thereby to form alpha-glycosyl ginsenoside.

The present invention is further illustrated by the following EXAMPLEs.

EXAMPLE 1

Syrup containing alpha-glycosyl ginsenoside

A seed culture of *Mucor javanicus* IFO 4570 was inoculated on 5 liters of a sterilized culture medium, consisting of 4 w/v % maltose, 0.1 w/v % $KH_2PO_4$, 0.1 w/v % $NH_4NO_3$, 0.1 w/v % $NaNO_3$, 0.05 w/v % $MgSO_4.7H_2O$, 0.05 w/v % KCl, 0.2 w/v % polypeptone, water, and 1 w/v % $CaCO_3$ (separately sterilized and added), and cultured thereon at 30° C. for 44 hours under aeration-agitation conditions. Four hundred and eighty g of the wet cells, obtained from the culture broth, was added with 5 liters of 4M urea solution in 0.5M acetate buffer (pH 5.3), and allowed to stand at 30° C. for 40 hours. Then, the supernatant was dialyzed against running tap water overnight, added with ammonium sulfate to bring 0.9 saturation, and allowed to stand at 4° C. overnight. After centrifugation, the resultant precipitate was suspended in 100 ml of acetate buffer (pH 6.0), and centrifuged to obtain a supernatant which was feasible as a solution of alpha-glucosidase (EC 3.2.1.20).

Sixty g of "KORAI-NINJIN EKISU", trade name of a commercial ginseng extract, available from Kanebo Pharmaceuticals Ltd, Tokyo, Japan, and 300 g of maltodextrin (DE 40) were dissolved together in 500 ml of a hot water, and the resultant solution was adjusted to 50° C. and pH 6.0, added with the alpha-glucosidase solution, and incubated for 24 hours to effect enzymatic reaction.

The reaction mixture was heated to inactivate the enzyme, followed by filtration. Then, the resultant filtrate was applied first on a column, packed with 5 g of "Columnlite", trade name of a commercial magnesia adsorbent, a product of Fuji Chemical Industries Incorporation, Ltd., Toyama-ken, Japan, to remove coloring impurities, then on a column of ion exchange resins, "Amberlite IR-120 B (H-form)" and "Amberlite IRA-94 (OH-form)" to effect deionization, followed by in vacuo concentration to obtain a syrup containing alpha-glycosyl ginsenoside having a moisture content of 20%. The overall yield was about 95% on the basis of dry solid.

This syrup is substantially free from unpleasant tastes, such as, bitter, astringent or harsh taste, but a mild sweetness. Thus, it may be ingested intact, or used in a food product.

EXAMPLE 2

Powder containing alpha-glycosyl ginsenoside

A seed culture of *Bacillus megaterium* FERM-P No. 935 was inoculated on 5 liters of a fresh culture medium having the same composition as used in EXPERIMENT 1—1, and cultured thereon at 28° C. for 3 days under aeration-agitation conditions. After completion of the cultivation, the culture broth was centrifuged to obtain a supernatant which was then added with ammonium sulfate to give 0.7 saturation, followed by an additional centrifugation to harvest a precipitate containing $3 \times 10^5$ units of cyclodextrin glucanotransferase activity as defined in EXPERIMENT 1—1.

Sixty g of "KORAI-NINJIN EKISU", trade name of a commercial ginseng extract, available from Lotte Bussan Co., Ltd., Tokyo, Japan, and 180 g of beta-cyclodextrin were dissolved together in 500 ml of water while heating. The resultant solution was cooled to 50° C., adjusted to pH 5.5, added with 15 units of the cyclodextrin glucanotransferase per g beta-cyclodextrin, and incubated at 50° C. and pH 5.5 for 24 hours to effect enzymatic reaction, followed by heat-inactivation of the enzyme. After filtering the reaction mixture, the resultant filtrate was applied on a column, packed with 3 liters of "Amberlite XAD-7", trade name of a commercial macroreticular resin, a product of Rohm & Haas company, Philadelphia, Pa., USA. The column was first washed with a sufficient water to remove free saccharides, thereafter charged with 10 liters of 50 v/v % aqueous ethanol solution. The eluate was concentrated, and dried to obtain about 21 g of a powder containing alpha-glycosyl ginsenoside.

The powder was chromatographed using a thin-layer plate similarly as Sample No. 5 in EXPERIMENT 3. As a result, a small ginsenoside-$Rb_2$ spot and a unseparable tailing were found at $R_f$ 0.52 and from origin to $R_f$ near 0.10 respectively. These spot and tailing appeared purple red.

Separately, the powder was first subjected to glucoamylase, then chromatographed, similarly as Sample No. 5. As a result, it was confirmed that, during the enzymatic reaction, the powder gradually hydrolyzes to give a series of purple red spots and a brown spot which correspond to ginsenoside-$Ro$, -$Rb_1$, -$Rb_2$, -$Rc$, -$Rd$, -$Re$, -$Rf$, -$Rg_1$, -$Rg_2$ and D-glucose respectively.

The powder is free from the unpleasant tastes, i.e. bitter, astringent or harsh taste. Thus, it may be ingested intact, or, if necessary, seasoned with a sweetener or sour prior to its use.

The powder was chromatographed on a silica gel column using a mixture of n-butanol, ethyl acetate and water (4:1:5) as a developing solvent, and the novel substance fraction tailing from origin to $R_f$ 0.10 was recovered, and dried into powder. This substance is a readily water-soluble and almost neutral substance which hardly tastes bitter, astringent or harsh. The substance is partially soluble in a low alcohol, such as methanol, ethanol or n-butanol, but hardly in chloroform or ethyl ether.

EXAMPLE 3

Syrup containing alpha-glycosyl ginsenoside

One kg of a dried ginseng, "HAKUJIN", was minced, added with 5 liters of 40 v/v % aqueous methanol solution, and allowed to soak overnight to effect extraction. After filtering to obtain an extract and residue, the latter was further extracted with the same amount of a fresh 40 v/v % aqueous methanol solution similarly as above, followed by harvest of another extract.

Both extracts were pooled, and concentrated in vacuo at below 50° C. to evaporate methanol. Sixty g of the resultant concentrate and 200 g of maltodextrin (DE 30) were dissolved together in 300 ml of water, added with 10 units of cyclodextrin glucanotransferase per g maltodextrin, and incubated for 24 hours while maintaining pH 5.5 and 60° C. to effect enzymatic reaction, followed by heat-inactivation of the enzyme. After filtering the reaction mixture, the resultant filtrate was concentrated to obtain about 300 g of a syrup containing alpha-glycosyl ginsenoside with a moisture content of 20%.

This syrup is substantially free from the unpleasant tastes, i.e. bitter, astringent or harsh tastes, but a mild sweetness. Thus, the syrup may be ingested intact, or used in a food product.

EXAMPLE 4

Syrup containing alpha-glycosyl ginsenoside

One kg of a dried ginseng, "KOHJIN", was minced, added with 5 liters of a 30 v/v % aqueous methanol solution, allowed to soak overnight at ambient temperature to effect extraction, and filtered to harvest an extract. The residue was added with the same amount of a fresh 30 v/v % aqueous ethanol solution, and allowed to soak to effect extraction, and filtered to obtain another extract, similarly as above.

These extracts were pooled, allowed to contact with a magnesia adsorbent to remove coloring impurities, deionized and purified with an ion exchange resin, and concentrated in vacuo to obtain about 50 g of a concentrate, similarly as in EXAMPLE 1.

A 1% seed culture of *Leuconostoc mesenteroides* IAM 1151 was inoculated on 10 liters of a culture medium, consisting of 50 g of the concentrate, 40 g of sucrose, 5 g of yeast extract, 8 g of $KH_2PO_4$, 24 g of $K_2HPO_4$, 0.2 g of $MgSO_4.7H_2O$, 0.2 g of $MnSO_4$ and water, and cultured thereon at 25° C. for 24 hours. After centrifuging the culture broth, the supernatant was added with 10 g of "M-511", trade name of a commercial magnesia adsorbent, product of Hokkaido Soda Company, Ltd., Tokyo, Japan, allowed to stand for 15 minutes under stirring conditions, and filtered, thereby to remove coloring impurities. Then, the filtrate was deionized by applying to ion exchange resins, "Amberlite IR-200 C (H-form)" and "Amberlite IRA-93 (OH-form)", and concentrated in vacuo to obtain an about 70 g of syrup containing alpha-glycosyl ginsenoside with a moisture content of 30%.

This syrup is substantially free from the unpleasant tastes, i.e. bitter, astringent or harsh taste. Thus, it may be ingested intact, or used in a food product.

Another portion of the seed culture was inoculated and cultured on a fresh medium of the same composition as above, except that the concentrate was neglected. After centrifuging the culture broth, the supernatant was added with a $CaPO_4$ gel, dialyzed, and subjected to centrifugation following harvest of $CaPO_4$ gel. The gel was then suspended in 0.2M $NaHPO_4$ solution (0.35 saturation, ammonium sulfate) to effect elution, and the eluate was concentrated to obtain 100 ml of a solution containing dextransucrase (EC 2.4.1.5) The solution was added to 100 ml of an aqueous solution containing 30 g of sucrose and 20 g of a concentrated ginseng extract, obtained similarly as above. The resultant mixture solution was subjected to enzymatic reaction at pH 5.3 and 30° C. for 16 hours, purified, and concentrated to obtain about 60 g of a syrup containing alpha-glycosyl ginsenoside. This syrup had properties similar to those as found in the hereinbefore described syrup.

The alpha-glycosyl ginsenoside constituent in this syrup was gradually hydrolyzed by isomaltodextranase (EC 3.2.1.94) to give ginsenoside and isomaltose. This suggests that one or more D-glucose moieties are bound to ginsenoside residue in alpha-1,6 fashion.

EXAMPLE 5

Syrup containing alpha-glycosyl ginsenoside

To 1 liter of water was added 300 g of potato starch, and 60 g of a concentrated ginseng extract, prepared by the method as described in EXAMPLE 3, and the resultant solution was adjusted to pH 6.0, added a commercial liquefying alpha-amylase (EC 3.2.1.1) of a bacterium origin, a product of Seikagaku Kogyo Co., Ltd., Tokyo, Japan, in an amount of 10 units per g starch in terms of the enzyme unit as defined in EXPERIMENT 1—1, and liquefied by heating to 80° C. under stirring conditions. After completion of the liquefaction, the resultant was cooled to 60° C., and subjected to a further enzymatic reaction for an additional 2 days. Similarly as in EXAMPLE 1, the reaction mixture was heated to inactive the alpha-amylase, filtered, purified with a magnesia adsorbent and ion exchange resins, concentrated in vacuo, dried, and pulverized to obtain a powder containing alpha-glycosyl ginsenoside. The overall yield was about 97% on the basis of dry solid.

This powder is substantially free from the unpleasant tastes, i.e. bitter, astringent or harsh taste, but a mild sweetness. Thus, it may be ingested intact, or used in a food product.

EXAMPLE 6

Sweetener

One kg of "FUNMATSU MABIT ®", trade name of a commercial crystalline maltitol powder, available from Hayashibara Shoji, Inc., Okayama, Japan, was admixed with 30 g of "α-G-Sweet", trade name of a commercial alpha-glycosyl stevioside, a product of Toyo Sugar Refining Co., Ltd., Tokyo, Japan, and 20 g of a syrup containing alpha-glycosyl ginsenoside, prepared by the method as described in EXAMPLE 1. The resultant admixture was placed and shaped in a mold by applying a slightly high pressure, and the content was released therefrom to obtain about 3 g cubic sweeteners.

The resultant is a sweetener containing alpha-glycosyl ginsenoside which may be advantageously usable for sweetening coffee, tea or soft drink to impart thereto with the inherent efficacy of ginsenoside, e.g. invigorating, peptic or haematic effect. Also, the product is suitable for use as a low-cariogenic sweetener, as well as for the use as a low-caloric sweetener.

EXAMPLE 7

Sweetener

Fifty g of a powder containing alpha-glycosyl ginsenoside, prepared by the method as described in EXAMPLE 2, was dissolved in 20 ml of water. To the solution was admixed with 1 kg of honey to obtain a sweetener containing alpha-glycosyl ginsenoside.

This sweetener may be ingested intact, or used for sweetening a health food or drink for beauty, as well as for improving the taste quality of a herb medicine.

EXAMPLE 8

Hard candy

Six kg of sucrose, 3 kg of "SUNMALT®", trade name of a crystalline maltose powder, a product of Hayashibara Company Ltd., Okayama, Japan, and 1 kg of a syrup containing alpha-glycosyl ginsenoside, prepared by the method as described in EXAMPLE 3, were dissolved in 5 liters of water while heating, and the resultant solution was boiled up at 145°–150° C., concentrated in vacuo while heating to give a moisture content below 2%. The resultant concentrate was admixed with 80 g of citric acid, and small amounts of lemon flavor and coloring agent, and shaped in usual way to obtain the titled product. The product is advantageously feasible for use as a hard candy which exhibits the inherent efficacy of ginsenoside, e.g. invigorating, anti-inflammatory or expectorant effect.

EXAMPLE 9

Chewing gum

After softening by heating, 2 kg of gum base was admixed with 7 kg of "FUNMATSU MABIT®", trade name of a commercial crystalline maltitol powder, available from Hayashibara Shoji, Inc., Okayama, Japan, 20 g of "α-G-Sweet", trade name of a commercial alpha-glycosyl stevioside, a product of Toyo Sugar Refining Co., Ltd., Tokyo, Japan, 300 g of a powder containing alpha-glycosyl ginsenoside, prepared by the method as described in EXAMPLE 5, and small amounts of menthol and coloring agent. The admixture was then kneaded with a roll, and shaped in usual way to obtain the titled product.

Since the product is excellent in texture and sweetness, it is advantageously feasible for use as a chewing gum which exhibits the inherent efficacy of ginsenoside, e.g. invigorating, haematic, anti-inflammatory or expectorant effect. Also, the product is suitable for use as a low-caloric or low-cariogenic chewing gum.

EXAMPLE 10

Chocolate

A composition, consisting of 40 kg of cacao paste, 10 kg of cacao butter, 15 kg of powdered sugar, 15 kg of whole milk powder, and 500 g of a powder containing alpha-glycosyl ginsenoside, prepared by the method as described in EXAMPLE 2, was admixed, and placed in a refiner to reduce its particle size. Thereafter, the content was transferred into a conche, added with 500 g lecithin, and kneaded at 50° C. for 2 days therein. Then, the content was placed in a shaping apparatus, and solidified therein to obtain the titled product.

The product is excellent in texture and flavor, and free from fat- or sugar-blooming during storage. Also, the product is suitable for use as a chocolate which exhibits the inherent efficacy of ginsenoside, e.g. invigorating, peptic or haematic effect.

EXAMPLE 11

Sour milk beverage

Ten kg of defatted milk was pasteurized at 80° C. for 20 minutes, cooled to 40° C., and added with 300 g of a starter, followed by 10-hour incubation at 35°–37° C. Thereafter, the resultant was homogenized, added with 9.6 kg of sucrose and 400 g of a syrup containing alpha-glycosyl ginsenoside, prepared by the method as described in EXAMPLE 4 using dextransucrase, andd kneaded sufficiently at 80°–85° C. under stirring conditions to effect pasteurization.

The mixture was cooled, admixed with a small amount of flavor, and bottled to obtain the titled product.

The product is suitable for use as an invigorating sour milk beverage.

EXAMPLE 12

Carbonated beverage

In 8 liters of water was dissolved 1.97 kg of a commercial isomerized sugar solution (conversion degree 55%), 12.5 g of a syrup containing alpha-glycosyl ginsenoside, prepared by the method as described in EXAMPLE 3, 23 g of citric acid, 0.2 g of vitamin $B_1$ sulfate and 0.5 g of vitamin $B_6$ while stirring, and the resultant solution was gassed with 2 volumes of carbon dioxide with the aid of a carbonator in usual way thereby to obtain the titled product.

The product is suitable for use as an invigorating drink.

EXAMPLE 13

Jelly

Three hundred g of prune extract (moisture content 30%), 2 kg of sucrose, 2 kg of glucose, 2 kg of corn syrup (moisture content 25%), 16 g of a syrup containing alpha-glycosyl ginsenoside, prepared by the method described in EXAMPLE 3, and 2.13 liters of water were admixed, and the mixture was boiled while heating and stirring to give a moisture content of 20%. The resultant was added with a hot aqueous solution (60° C.), wherein 350 g of "Yellow Ribbon", trade name of a commercial high-methoxyl pectin, available from Yukijirushi Shokuhin KK, Tokyo, Japan, was dissolved to give a concentration of 5 w/w %, boiled while heating until its moisture content reached 22–23%, added with 200 g of 50 w/w % aqueous citric acid solution under vigorous stirring conditions, poured into a mold at a temperature above 90° C., and solidified therein by 8 hour-standing under ambient conditions. The content was removed therefrom, dried by ventilation of 40° C. air, and packaged to obtain the titled product.

The product is a jelly excellent in biting properties. Also, it is suitable for use as an invigorating jelly.

EXAMPLE 14

Jelly

A composition of 1.5 kg of sucrose, 30 g of sodium citrate, 110 g of "GF-10", trade name of a commercial stabilizer, product of Nitta Gelatine Co., Ltd., Osaka, Japan, 12.5 g of a syrup containing alpha-glycosyl ginsenoside, prepared by the method as described in EXAMPLE 3, and 7.3 liters of water, was admixed while heating. The resultant admixture was then kept at 80° C. for 10 minutes, and further admixed with 1 kg of prune extract (moisture content 30%) and 30 g citric acid, dissolved in a minimum amount of water, while stirring. The resultant was packed in a vessel at 60°–70° C., sterilized at 90° C. for 30 minutes, and cooled to obtain the titled product.

The product is a jelly having a refreshing taste and sweetness. Also, the product is suitable for use as an invigorating or haematic jelly.

EXAMPLE 15

"TSUKUDANI"

Two hundred and fifty g of tangle was treated to remove the sand, soaked in acid solution, and cut into squares, in usual way. Thereafter, the tangle was soaked in a mixture solution, consisting of 212 ml soy sauce, 318 ml amino acid solution, 30 g of sucrose, 20 g of corn syrup, 1 g of pullulan and 10 g of a syrup containing alpha-glycosyl ginsenoside, prepared by the method as described in EXPERIMENT 1-2 for Sample No. 4. While boiling, the mixture was further added with 12 g of monosodium glutamate, 8 g of caramel and 21 ml of "MIRIN"—a type of Japanese-style liquor, and boiled up to obtain the titled product, "TSUKUDANI"—a type of Japanese-style preserved food.

The product is an appetizing "TSUKUDANI" with an excellent color, gloss, appearance, flavor and taste. Also, the product is suitable for use as an invigorating "TSUKUDANI".

EXAMPLE 16

Pickled scallion

Five kg of raw scallion was soaked in 2.5 liters of an about 20% aqueous sodium chloride solution for 3 weeks. After draining off the water, the scallion was pickled for 1 month in an acetic acid solution, consisting of 2.0 liters of water, 80 ml of glacial acetic acid and 80 g of sodium chloride. Then, the scallion was soaked for 10 days in a seasoning solution, consisting of 800 ml of vinegar, 40 ml of "MIRIN"—a type of Japanese-style liquor, 10 g of caynne-pepper, and 5 g of a powder containing alpha-glycosyl ginsenoside, prepared by the method as described in EXAMPLE 2, thereby to obtain a tasty pickled scallion excellent in flavor, and suitable for use as an invigorating food.

EXAMPLE 17

Tablet

A mixture, consisting of 100 g of "SUNMALT®", trade name of a commercial crystalline maltose powder, product of Hayashibara Co., Ltd., Okayama, Japan, 10 g of corn starch, and a powder containing alpha-glycosyl ginsenoside, prepared by the method as described in EXAMPLE 5, was sufficiently kneaded. Then, the mixture was shaped with the use of a tabletting machine, equipped with 20 R-punch of 12 mm diameter, into tablet of 680 mm each, 5.25 mm thick and 8±1 kg hardness. The product is an easily administrable tablet having the inherent efficacies of ginsenoside, e..g. invigorating, peptic, intestine-regulating, haematic, anti-inflammatory or expectorant effect.

EXAMPLE 18

Dentifrice

A dentifrice was prepared by kneading a composition with a formulation of $CaHPO_4$, 45%; pullulan, 2.75%; sodium laulyl sulfate, 1.5%; glycerine, 18.0%; polyoxyethylene solbitan monolaulate, 0.5%; antiseptic agent, 0.05%; "α-G-Sweet", trade name of a commercial alpha-glycosyl stevioside, product of Toyo Sugar Refining Co., Ltd., Tokyo, Japan, 0.2%; a powder containing alpha-glycosyl ginsenoside, prepared by the method as described in EXAMPLE 2, 2.0%; and water, 30.0%, in usual way.

The product is suitable for use as a dentifrice which exhibits anti-inflammatory or expectorant effect.

While specific details have been shown and described, it should be understood that changes and alterations may be resorted to without departing from the spirit of the invention as defined in the appended claims.

What is claimed is:

1. A composition of the structure selected from the group consisting of:

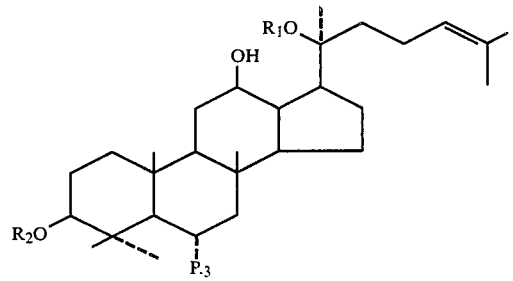

and

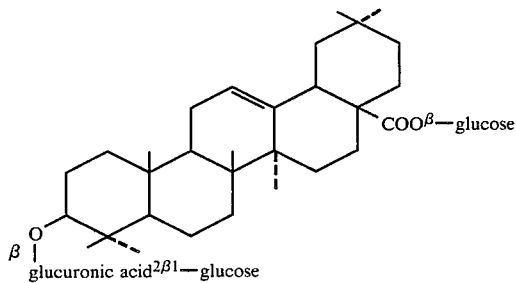

wherein:
a. $R_1 = -\beta\text{glucose-}^{6\beta 1}\text{glucose}$, $R_2 = -\beta\text{glucose-}^{2\beta 1}\text{glucose}$, $R_3 = H$;
b. $R_1 = -\beta\text{glucose-}^{6\alpha 1}\text{arabinopyranose}$, $R_2 = -\beta\text{glucose-}^{6\alpha 1}\text{glucose}$, $R_3 = H$;
c. $R_1 = -\beta\text{glucose-}^{6\alpha 1}\text{arabinofuranose}$, $R_2 = -\beta\text{glucose-}^{2\beta 1}\text{glucose}$, $R_3 = H$;
d. $R_1 = -\beta\text{glucose}$, $R_2 = -\beta\text{glucose-}^{2\beta 1}\text{glucose}$, $R_3 = H$;
e. $R_1 = -\beta\text{glucose}$, $R_2 = H$, $R_3 = -O-\beta\text{glucose-}^{2\alpha 1}\text{rhamnose}$;
f. $R_1 = R_2 = H$, $R_3 = -O-\beta\text{glucose-}^{2\beta 1}\text{glucose}$;
g. $R_1 = -\beta\text{glucose}$, $R_2 = H$, $R_3 = -O-\beta\text{glucose}$; and
h. $R_1 = R_2 = H$, $R_3 = -O-\beta\text{glucose-}^{2\alpha 1}\text{rhamnose}$.

2. The compound as set forth in claim 1, whenever prepared by:
providing an aqueous solution containing 0.1–30 w/w % ginsenoside and 1–50 w/w % of a member sected from the group consisting of maltooligosaccharides, liquefied starch, partial starch hydrolysate, sucrose, and mixtures thereof; and
subjecting the solution to an alpha-glucosyl transferase at a pH in the range of 3–10 and a temperature in the range of 20°–80° C. to form the compound.

3. The compound as set forth in claim 2, wherein the alpha-glucosyl transferase is a member selected from the group consisting of alpha-glucosidase, alpha-amylase, cyclodextrin glucanotransferase, dextransucrase, dextran dextrinase, and amylosucrase.

4. The compound as set forth in claim 2, wherein the weight ratio of ginsenoside to the alpha-glucosyl saccharide is in the range of 0.5–300 on the basis of dry solid.

* * * * *